(12) United States Patent
Malmin et al.

(10) Patent No.: US 7,968,852 B1
(45) Date of Patent: Jun. 28, 2011

(54) MITIGATION OF ERRORS IN AN IMAGING SYSTEM WITH DETECTORS MOUNTED TO A GANTRY AND ROTATABLE THEREON

(75) Inventors: Ronald E. Malmin, Chicago, IL (US); Manjit Ray, Hoffman Estates, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 0 days.

(21) Appl. No.: 12/887,863

(22) Filed: Sep. 22, 2010

(51) Int. Cl.
*H01L 27/146* (2006.01)
(52) U.S. Cl. .................................. 250/370.09
(58) Field of Classification Search ............ 250/370.01–370.15, 363.01–363.1, 362; 378/98.8, 20
See application file for complete search history.

(56) References Cited

U.S. PATENT DOCUMENTS

| | | | | |
|---|---|---|---|---|
| 4,385,397 A | * | 5/1983 | Verro | 378/20 |
| 2007/0075250 A1 | * | 4/2007 | Malmin | 250/363.08 |

OTHER PUBLICATIONS

Metzler et al., "Measuring the variation in radius of rotation as a function of gantry angle for ultra-high-resolution pinhole SPECT," 2005, IEEE Transactions on Nuclear Science, vol. 52, No. 5, pp. 1236-1242.*

* cited by examiner

*Primary Examiner* — David P. Porta
*Assistant Examiner* — Kiho Kim
(74) *Attorney, Agent, or Firm* — Peter L. Kendall

(57) ABSTRACT

Implementations of the present technology include error mitigation processes that determine gantry angle-dependent measures of detector deflections for a given class of systems using a first method, then determine gantry angle-independent deviations from the class measures using a second method on a specific system; then apply, to the specific system of the second method, the gantry angle-dependent class deflection results of the first method modified by the system-specific gantry angle independent deflections of the second method; and further include a system calibrated by such combinations of processes and computer program products for performing at least portions of the combination of processes.

15 Claims, 7 Drawing Sheets

Optotrack / Fixed-Scanner Coordinate System

MITIGATION OF ERRORS IN AN IMAGING SYSTEM WITH DETECTORS MOUNTED TO A GANTRY AND ROTATABLE THEREON

FIELD

The technology disclosed herein (the "technology") relates to, inter glia, imaging systems, and, in particular, to error mitigation processes in such systems, systems that mitigate errors by such processes, and computer program products for performing at least portions of the processes.

BRIEF DESCRIPTION OF THE DRAWINGS

Reference will now be made, by way of example, to the accompanying drawings which show example implementations of the present application.

DETAILED DESCRIPTION

Reference will now be made in detail to implementations of the technology. Each example is provided by way of explanation of the technology only, not as a limitation of the technology. It will be apparent to those skilled in the art that various modifications and variations can be made in the present technology without departing from the scope or spirit of the technology. For instance, features described as part of one implementation can be used on another implementation to yield a still further implementation. Thus, it is intended that the present technology cover such modifications and variations that come within the scope of the technology.

Medical imaging technology may be used to create images of the human body for clinical purposes (e.g., medical procedures seeking to reveal, diagnose or examine disease) or medical science (including the study of normal anatomy and physiology). Medical imaging technology includes: radiography including x-rays, fluoroscopy, and x-ray computed axial tomography (CAT or CT); magnetic resonance imaging (MRI); and nuclear medical imaging such as scintigraphy using a gamma camera, single photon emission computed tomography (SPECT), and positron emission tomography (PET).

In nuclear medicine imaging, radiopharmaceuticals are taken internally, for example intravenously or orally. Then, external systems capture data from the radiation emitted, directly or indirectly, by the radiopharmaceuticals; and then form images from the data. This process is unlike a diagnostic X-ray where external radiation is passed through the body and captured to form an image.

Figure 1:
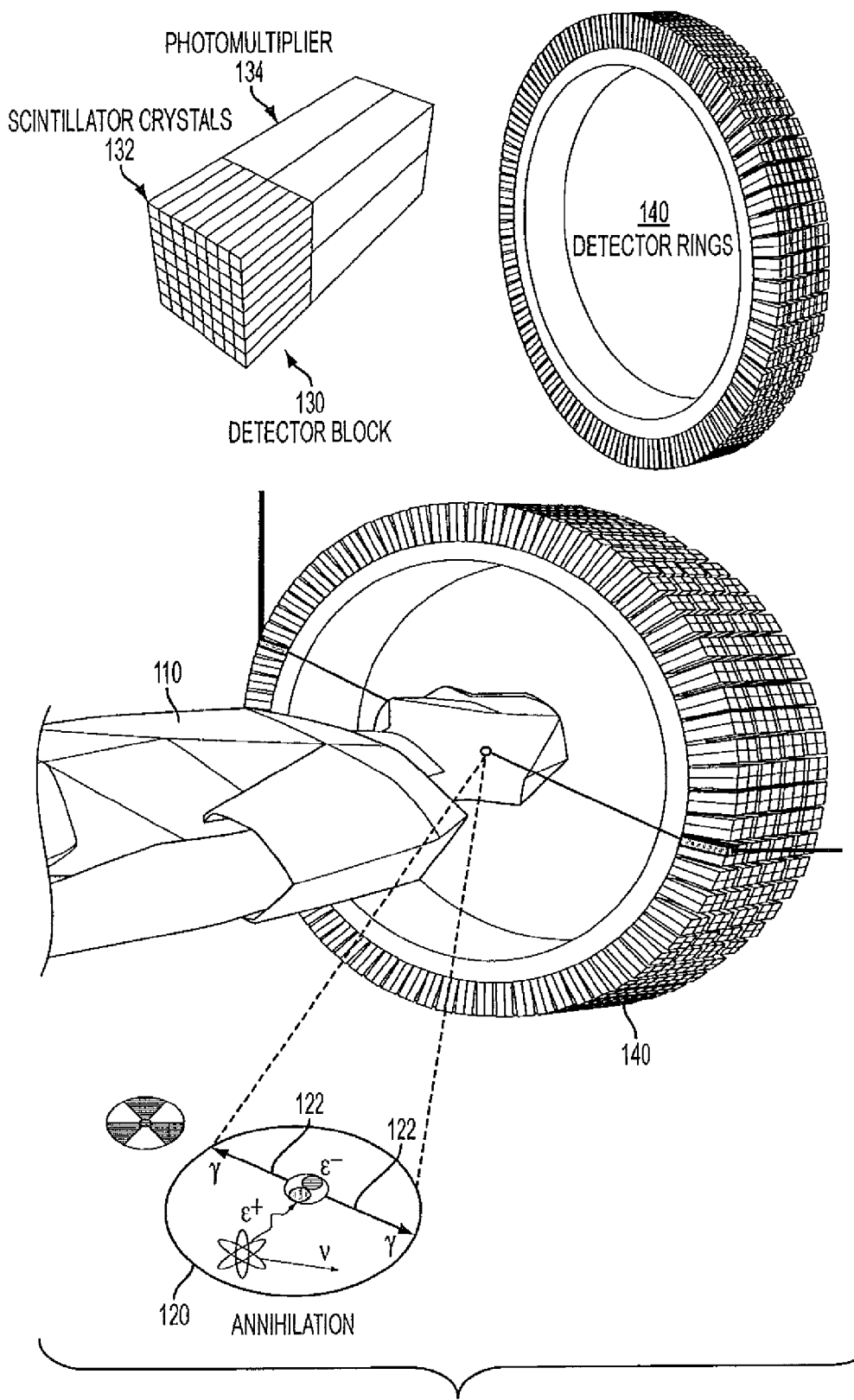
FIG. 1 illustrates a Positron Emission Tomography (PET) system having fixed detector blocks.

Referring to FIG. 1, in PET, a short-lived radioactive tracer isotope is injected or ingested into the subject 110. As the radioisotope undergoes positron emission decay 120 (also known as positive beta decay), it emits a positron, an antiparticle of the electron with opposite charge. The emitted positron travels in tissue for a short distance, during which time it loses kinetic energy, until it decelerates to a point where it can interact with an electron. The encounter annihilates both electron and positron, producing a pair of annihilation (gamma) photons 122 moving in approximately opposite directions. These are detected when they reach a scintillator 132 in the scanning device, creating a burst of light which is detected by photomultiplier tubes 134 or silicon avalanche photodiodes (Si APD). The PET detector blocks 130 are typically fixed in a detector ring 140.

SPECT imaging is performed by using a gamma camera (similar to a PET detector block) to acquire multiple 2-D images (also called projections), from multiple angles. SPECT is similar to PET in its use of radioactive tracer material and detection of gamma rays. In contrast with PET, however, the tracer used in SPECT emits gamma radiation that is measured directly, whereas PET tracer emits positrons which annihilate with electrons up to a few millimeters away, causing two gamma photons to be emitted in opposite directions. A PET scanner detects these emissions "coincident" in time, which provides more radiation event localization information and thus higher resolution images than SPECT. SPECT scans, however, are significantly less expensive than PET scans, in part because they are able to use longer-lived more easily-obtained radioisotopes than PET. Therefore, technology that increases the accuracy of SPECT is desirable.

Figure 2:
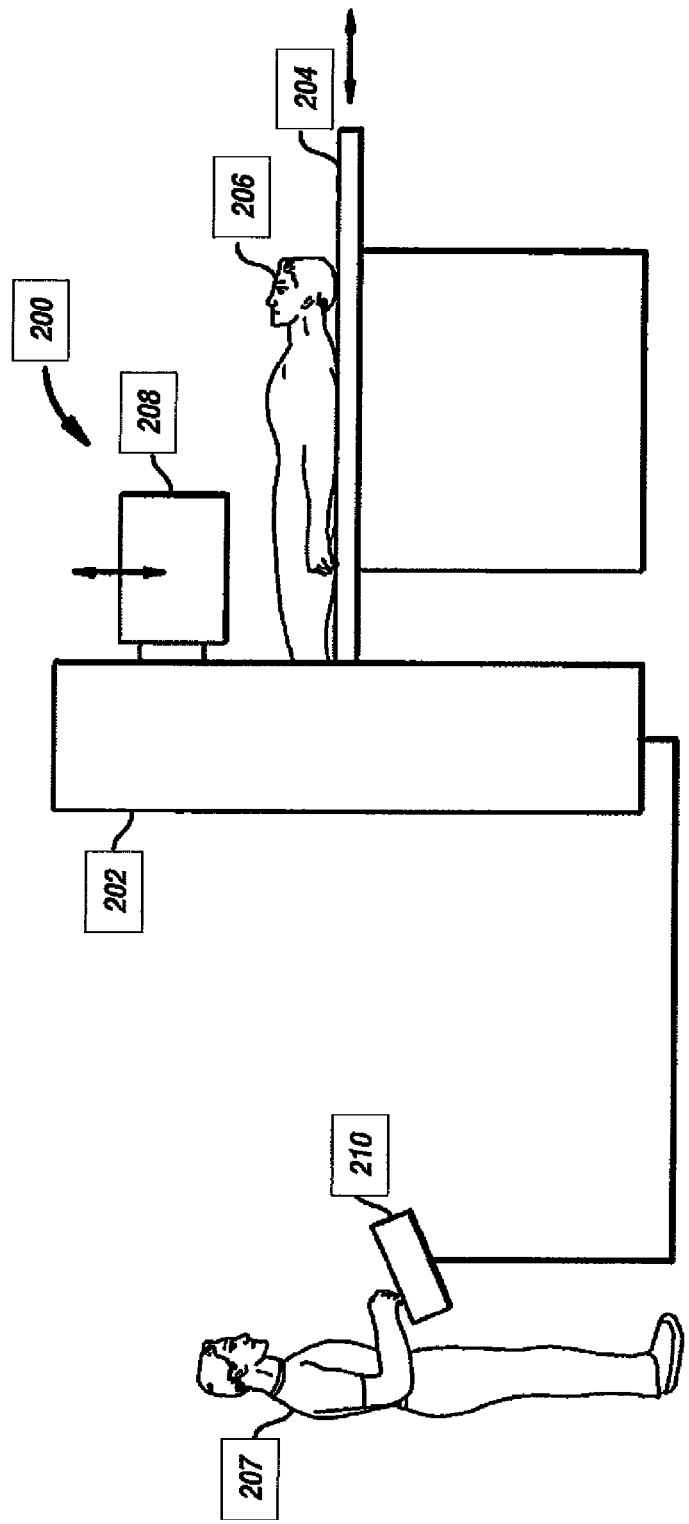
FIG. 2 illustrates an imaging system, e.g., Single Photon Emission Computed Tomography (SPECT) system having detector blocks rotatable about a gantry.

FIG. 2 depicts components of a typical SPECT system 200 (i.e., having a gamma or scintillation camera) which includes a gantry 202 supporting one or more detectors 208 enclosed within a metal housing and movably supported proximate a patient 206 located on a patient support (e.g., pallet or table) 204. Typically, the positions of the detectors 208 can be changed to a variety of orientations to obtain images of a patient's body from various angles and locations along the patient's body. In many instances, a data acquisition console 210 (e.g., with a user interface and/or display) is located proximate a patient during use for a technologist 207 to manipulate during data acquisition. In addition to the data acquisition console 210, images are often "reconstructed" or developed from the acquired image data ("projection data") via a processing computer system that is operated at another image processing computer console including, e.g., an operator interface and a display, which may often be located in another room, to develop images. By way of example, the image acquisition data may, in some instances, be transmitted to the processing computer system after acquisition using the acquisition console.

To acquire SPECT images, the gamma camera is rotated around the patient on a gantry. Projections are acquired at defined points during the rotation, typically every 3-6 degrees. In most cases, a full 360 degree rotation is used to obtain an optimal reconstruction. The time taken to obtain each projection is also variable, but 15-20 seconds is typical. Groups of projections are taken successively as the patient 206 on the table 204 is moved incrementally through the gantry 202 through the region of the patient 206 to be imaged. This gives a typical total scan time of 15-20 minutes. Multi-headed gamma cameras can provide accelerated acquisition. For example, a dual headed camera can be used with heads spaced 180 degrees apart, allowing two projections to be acquired simultaneously, with each head requiring 180 degrees of rotation. Triple-head cameras with 120 degree spacing are also used.

A computer is then used to apply a tomographic reconstruction algorithm to the multiple projections, yielding a 3-D dataset. This dataset may then be manipulated to show thin slices along any chosen axis of the body, similar to those obtained from other tomographic techniques, such as MRI, CT, and PET.

Typical existing reconstruction algorithms implicitly assume that the axis normal to the each detector face (i.e., the central normal axis) is orthogonal to the axis of rotation (AOR) about which the gantry and detectors rotate. It further assumes that the detector (imaging) axis pointing in the "axial" direction is perfectly parallel to the AOR at all rotation angles. It also assumes rigid rotation.

With these assumptions, reconstruction of a full 3-D volume can be performed using individual 2-D projection data from each of a large number of gantry or projection angles θ. These assumptions, however, are not necessarily true. Among other things, mechanical tolerances and variation in assembly can produce misalignments of gantry components. In addition, gravity can produce mechanical deflections and these deflections can change with the rotation angle or position of the detector. Rotation is not rigid because of gravity.

SPECT reconstructions may include the some effects of non-ideal gantry/detector geometry into the reconstruction process. Previously, the effects of these misalignments on the reconstructed resolution had been masked by the dominant effect of other factors limiting accuracy and resolution, e.g., collimator resolution, with reconstructed resolution approximately equal to the attenuation-weighted average of collimator resolution in the projections. In this regime, only "zero-order" corrections for detector misalignments had been utilized, for example Center Of Rotation (COR) and Multi Head Registration (MHR).

Typical tomographic reconstructions rely on COR and MHR calibration schemes to mitigate some errors in the alignment of gantry/detector systems. These schemes can mitigate the effects of certain misalignments (e.g., translational offsets and the average effects of angular misalignments). Such "correctable" alignment error components can be accounted for by shifting the projection data before or during reconstruction and by adjusting the angle at which the data are back projected. Other components of resolution loss are not amenable to being removed by simple manipulation of the projection data because the misalignment causes effects whose magnitude varies depending on the distance from the axis of rotation and are blurred together during the projection acquisition. That is, the image of a point source in such systems oscillates axially in the projection images and the amplitude and phase of the oscillation depends on the location of the source within the object. This leads to blurring in the axial dimension in the tomographic reconstructions. For gantries with cantilevered heads, this is a particular problem because of head droop. Head droop can cause difficult-to-correct axial blurring, which not only can distort sagital and coronal images, but also can reduce contrast in transaxial images (because the counts are misplaced into other slices). In addition, reducing head droop via more rigid mechanics is expensive.

But recently, technologies such as molecular imaging and FLASH 3D reconstruction (resolution recovery) can offer higher resolution systems. Iterative reconstruction algorithms (such as, e.g., FLASH 3D) are capable of resolution recovery because they can include the physics of the acquisition process within the reconstruction algorithm, e.g., attenuation, scatter, and especially collimator resolution. In the context of such higher resolution technologies, the error sources described above can be significant enough to affect performance, and techniques such as COR and MHR as previously practiced are insufficient to take advantage of the highest resolutions available.

U.S. Pat. No. 7,655,913 ("the '913 patent"), hereby incorporated herein by reference, discloses technology for characterizing detector pitch, roll, and yaw misalignment an imaging unit that includes at least one cantilevered detector mounted on a gantry; and then using the characterization to mitigate the effects of misalignment on image reconstruction for that unit. Note that the '913 patent uses a coordinate reference system that labels the central imaging axis as "Y," while the present disclosure labels that axis as Z. As disclosed in the '913, pitch, roll, and yaw detector deflection errors that are substantially a function of angle of deployment of a detector around a gantry ("gantry angle"), and due at least in part to the effects of gravity on the detector head.

Gravity errors show a regular behavior as a function of gantry angle, and have been found to be substantially the same across units of the same detector/gantry configuration class. Errors, both orientation (pitch, roll, and yaw) and translation, from other causes have been found to be substantially constant with gantry angle and variable unit to unit. These unit-specific errors may be from misalignment and part tolerances. The optical measurement error correction technology described in the '913 process can mitigate each type of error (gravity error, non-gravity error) if the technology is applied to each unit. However, it would be resource intensive (both in time and money) to apply that technology to each unit.

Implementations of the present technology include error mitigation processes that determine gantry angle-dependent measures of detector deflections for a given class of systems using a first method, then determine gantry angle-independent deviations from the class measures using a second method on a specific system; then apply, to the specific system of the second method, the gantry angle-dependent class deflection results of the first method modified by the system-specific gantry angle independent deflections of the second method; and further include a system calibrated by such combinations of processes and computer program products for performing at least portions of the combination of processes.

Figure 3:
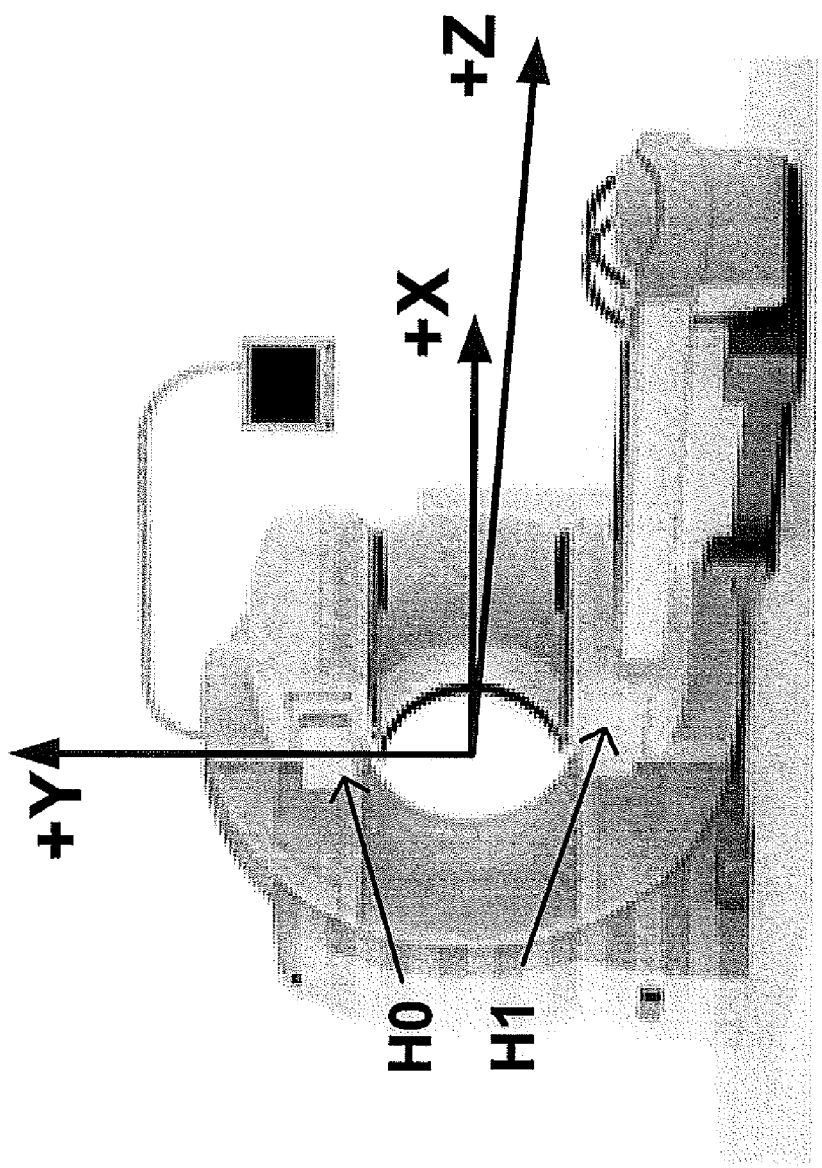
FIG. 3 illustrates a coordinate system convention used in conjunction with implementations of the present technology.

In some implementations of the technology, gantry angle-dependent deflections can be measured for a class of systems; where systems of the class have substantially identical gantry/detector configurations (e.g., the "class" being a model such as the Siemens Symbia T, with individual Symbia T units being the "system"). In such implementations, the gantry angle-dependent deflections for each of a plurality of units of that class, e.g., a sample of thirteen (13) systems, is determined. Referring to FIG. 3, a coordinate system aligned with the patient coordinate system (PCS) 300 can be used. In those implementations, detector pitch (rotation about the detector X axis), yaw (rotation about the detector Y axis), and roll (rotation about the detector Z axis), and translation along the three detector axes from the ideal center of the detector position ($\Delta x$, $\Delta y$, $\Delta z$) are measured for each system in the sample.

Figure 4:
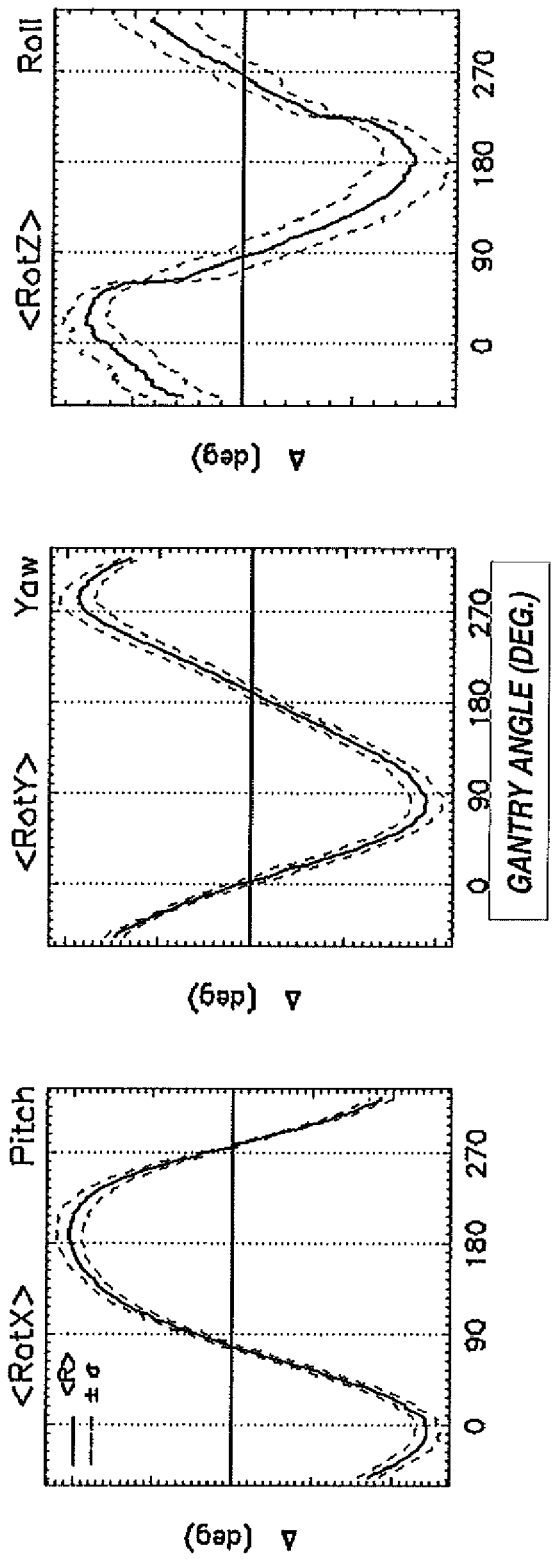
FIG. 4 illustrates Gantry Deflection Functions (GDF) for pitch, yaw, and roll of a detector head.
Figure 5:
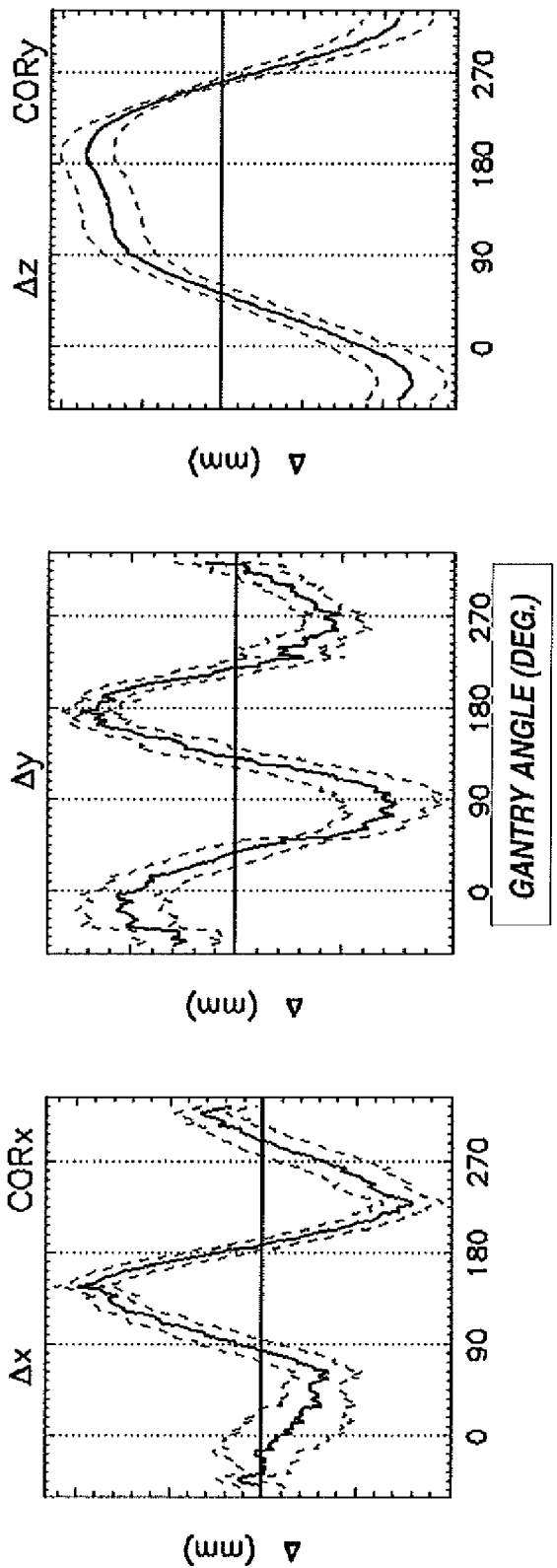
FIG. 5 illustrates Gantry Deflection Functions (GDF) for Δx, Δy, and Δz of a detector head.

FIG. 4 and FIG. 5 show the zero-mean average gantry deflection as a function of gantry angle, i.e., Gantry Deflection Function (GDF), obtained over thirteen (13) units of the same model. Using the zero-mean average can remove unit-specific angle-constant deflections from the GDF, making it applicable to all units of that class/model that have the same gantry/detector configuration. FIG. 4 shows the rotational deflections pitch, roll, and yaw. FIG. 5 shows the translations deflections $\Delta x$, $\Delta y$, and $\Delta z$. The deflections were obtained by using a precision optical system (at least 1 mm accuracy) such as OPTOTRACK of NORTHERN DIGITAL, INC. as described in the '913 patent. The solid line, e.g., 410 represents the zero mean average across the ten (10) units, the dashed lines 420 430 represent the $+1\sigma/-\sigma$ across the thirteen

(13) units. These deflections can be used as angle-dependent GDF for each system of that model. If it is found that the angle-average GDF is not zero but, rather, has a bias with smaller variance about that bias, the GDF for the class can be defined as the raw angle average, including bias.

Implementations of the present technology also determine the non-angle-dependent components of gantry deflection for each specific system/unit within a class of units. The non-angle-dependent components of gantry deflection are characterized by a vector, $\Delta$GDF, of six angle-independent offsets corresponding to the six parameters (pitch, roll, yaw, $\Delta x$, $\Delta y$, $\Delta z$) of the GDF of the class to which the specific system/unit belongs.

The $\Delta$GDF can be determined tracking point source sinograms (location versus angle) and standard non-linear least squares fitting. The spatial locations of the points are part of the parameter set to be fitted. In some implementations, five (5) point sources can be used. These 15 parameters (the x, y, and z coordinates of each of five point sources) can be reduced to six (6) parameters by constraining the points to a fixture with known relative locations of the sources. The reduced source location fit parameters are then the three (3) spatial coordinates of the fixture center and its three (3) Euler angles relative to the scanner coordinate system. For a two-headed system, point source calibration data from both detectors are simultaneously fit, as are the measured x and y positions. The technology can determine the point locations by point tracking using the system itself and then fitting these measured point "sinograms" to a model of the sources constrained to a fixture and viewed by a pair of detectors mounted on a gantry whose class standard deflection errors are described by a GDF.

In some implementations, the technology can determine the locations of the source points in the following fashion.

Figure 6:
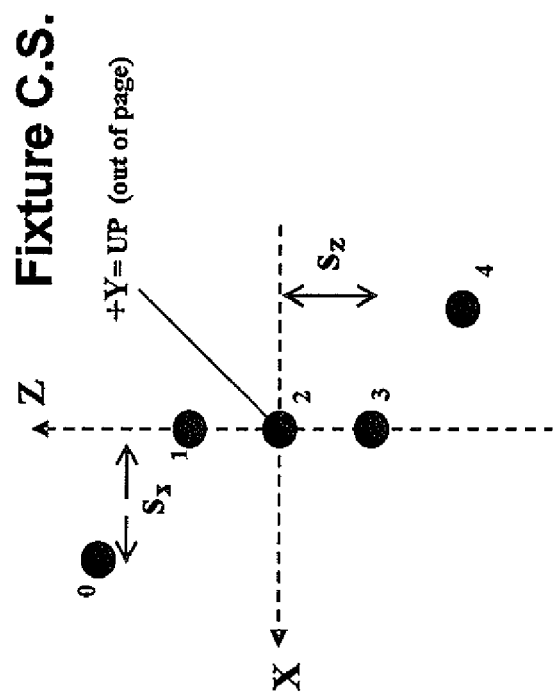
FIG. 6 illustrates a fixture coordinate system used in conjunction with implementations of the present technology.
Figure 7:
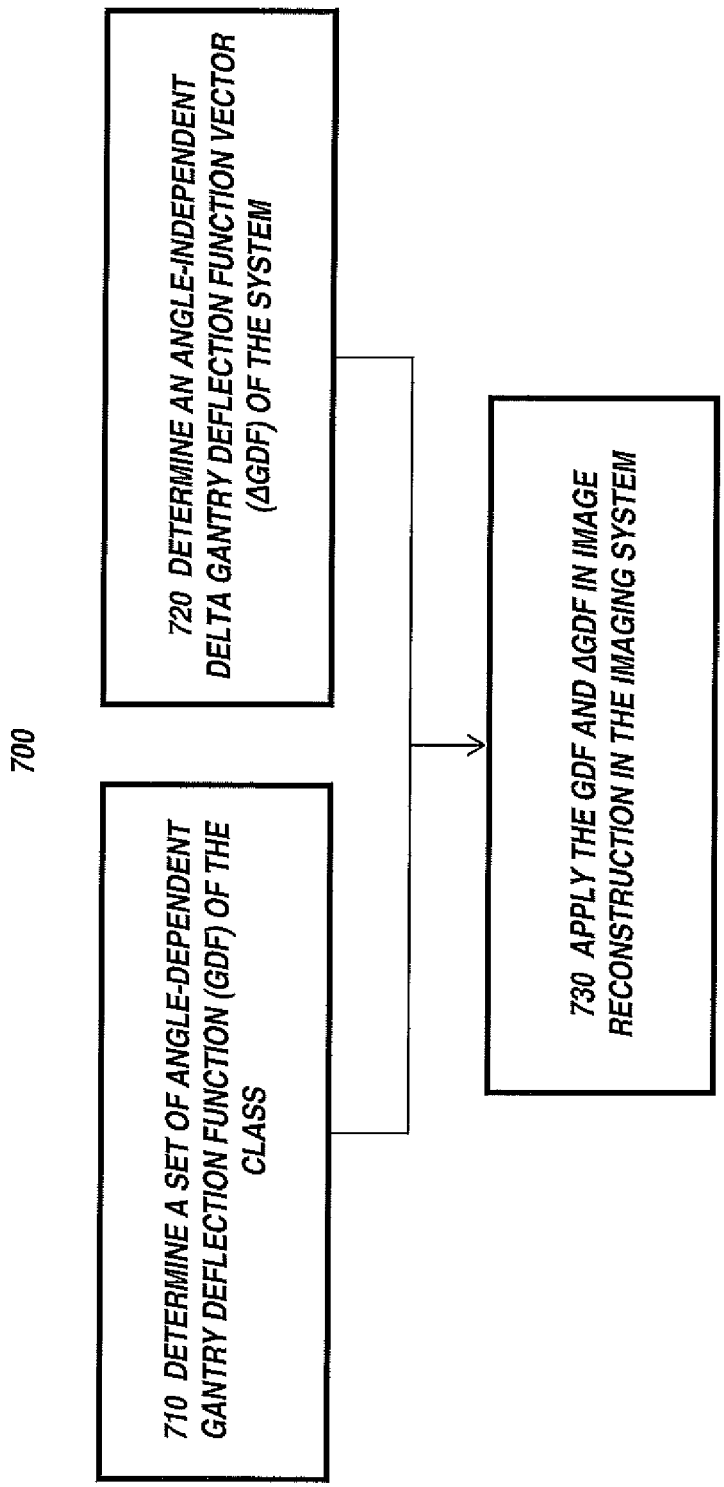
FIG. 7 illustrates methods of the technology.

The position matrix $R_{PTS}$ of source points constrained in a fixture at predetermined spacings relative to the fixture center can be defined. The Fixture Coordinate System (FCS), shown in FIG. 6 can be defined such that it is aligned and centered with the Patient CS (PCS). The points can be transformed from their Fixture CS coordinates to their actual locations in the Patient CS. This can be affected by a homogenous 4×4 transformation matrix. The three rotation and three translation parameters of this transformation can be the free fit variables. The points are now in their "true" spatial location in the Patient CS, e.g., $R_{PAT} = T_{FIX} \cdot R_{FTS}$.

Point locations from Patient CS can be transformed to gantry/fixed scanner CS, e.g., [x, y, z] centered axially at the detector center; $R_{SCAN} = \text{Rot}_{GDF} \cdot R_{PAT}$. This can be accomplished by constructing the rotation matrix, $\text{Rot}_{GDF}$, that expresses the coordinates of a vector (e.g., location of a source point) defined in the space-fixed scanner/Optotrack CS as seen in a detector CS that has been sequentially rotated by the gantry deflection function (GDF) errors (class GDF plus $\Delta$GDF). The rotation order is roll (@Z), yaw (@Y) pitch (@X). Giving standard Euler rotations as: $\text{Rot}_{GDF} = \text{RotX}'' \cdot \text{RotY}' \cdot \text{RotZ}$. Note that this includes standard macroscopic gantry rotation in the scanner roll error, and that the roll error adds to the scanner angle.

GDF translational shifts (plus offset fit variables) can be applied along the final transformed X''', Y''', Z''' axes. Y''' is normal to the detector surface (at whatever angle the gantry is positioned). Z''' points almost parallel the AOR (slightly skew because of the presumably small RotX and RotY). X''' is orthogonal to Y''' & Z'''

The shift along the Y axis of the rotating scanner CS orthogonal to axis of rotation Z (the "ROR" shift), can be applied, giving projections onto the transformed axes as: $\Delta \text{ROR}''' = -\text{Rot}_{GDF} \cdot [0, -\text{ROR}, 0]$.

The point locations are now properly defined within the detector-scanner coordinate system; i.e., as seen by the raw detector in the Scanner CS. The results can now be transformed from Scanner CS back to the Patient CS in order to compare to acquisition data.

The unit-specific fit parameter can now be computed based on the differences between measured sinograms and those predicted by the generic GDFs and constant offset $\Delta$GDF. Standard minimization techniques such as those of Marquardt can be used.

The technology can incorporate angle dependent class GDFs, e.g., measured with Optotrack, and includes an additive constant, specific to a given detector, for each angular function. It can fit the six degrees-of-freedom of the fixture location in space, while constraining the location of the points on the fixture, reducing the number of ancillary fit parameters, e.g., from fifteen (15) to six (6) for a five (5) source point fixture. It can fit multiple heads simultaneously. It can fit X- and Y-dimensional point locations simultaneously. For a two-headed gantry it can fix the initial angle of head 1 (base 0) to be zero and allow for an error in the relative angle between head 0 relative to head 1. It can extracts the average (DC) shifts in the angular values of roll ($\theta Z$), yaw($\theta Y$), and pitch ($\theta X$). It can extracts the additive average (DC) shifts in the translational error values of the detector ($\Delta X'''$, $\Delta Y'''$, $\Delta Z'''$).

In addition to the constant offsets to the GDFs, the technology can be extended to incorporate linear scale factors on the GDF values to account for collimators of different weight, since the amplitudes of the gantry deflections are observed to be linear, e.g., obey Hooke's Law.

Referring to FIG. 8, methods of the technology for mitigating detector position errors in an imaging system are illustrated. In such methods the imaging system comprises at least one detector connected to a gantry, and rotatable about the gantry. Further the imaging system is a member of a class of imaging systems having the same detector/gantry configuration.

In such methods a set of angle-dependent gantry deflection function (GDF) of the class is determined 810. An angle-independent delta gantry deflection function vector ($\Delta$GDF) of the system, each vector component corresponding to one of the GDF's, is determined 820. The GDF and $\Delta$GDF are applied in image reconstruction in the imaging system 830.

In some embodiments, each angle-dependent GDF comprises a zero-mean function. In some embodiments, the $\Delta$GDF is determined with respect to a plurality of point sources using the imaging system. In some of those embodiments, the plurality of point are contained in a fixture, and the $\Delta$GDF with respect to the plurality of point sources using the imaging system is determined with respect to a reference point on the fixture and the Euler angles of the point with respect to the imaging system coordinate system.

The present technology can take the forms of hardware, software or both hardware and software elements. In some implementations, the technology is implemented in software, which includes but is not limited to firmware, resident software, microcode, a Field Programmable Gate Array (FPGA), graphics processing unit (GPU), or Application-Specific Integrated Circuit (ASIC), etc. In particular, for real-time or near real-time use, an FPGA or GPU implementation would be desirable.

Furthermore, the present technology can take the form of a computer program product comprising program modules accessible from computer-usable or computer-readable medium storing program code for use by or in connection with one or more computers, processors, or instruction execution system. For the purposes of this description, a computer-usable or computer readable medium can be any apparatus that can contain, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium (though propagation mediums in and of themselves as signal carriers are not included in the definition of physical computer-readable medium). Examples of a physical computer-readable medium include a semiconductor or solid state memory, magnetic tape, a removable computer diskette, a random access memory (RAM), a read-only memory (ROM), a rigid magnetic disk and an optical disk. Current examples of optical disks include compact disk—read only memory (CD-ROM), compact disk—read/write (CD-R/W) and DVD. Both processors and program code for implementing each as aspect of the technology can be centralized or distributed (or a combination thereof) as known to those skilled in the art.

A data processing system suitable for storing a computer program product of the present technology and for executing the program code of the computer program product will include at least one processor coupled directly or indirectly to memory elements through a system bus. The memory elements can include local memory employed during actual execution of the program code, bulk storage, and cache memories that provide temporary storage of at least some program code in order to reduce the number of times code must be retrieved from bulk storage during execution. Input/output or I/O devices (including but not limited to keyboards, displays, pointing devices, etc.) can be coupled to the system either directly or through intervening I/O controllers. Network adapters can also be coupled to the system to enable the data processing system to become coupled to other data processing systems or remote printers or storage devices through intervening private or public networks. Modems, cable modem and Ethernet cards are just a few of the currently available types of network adapters. Such systems can be centralized or distributed, e.g., in peer-to-peer and client/server configurations. In some implementations, the data processing system is implemented using GPUs, FPGAs and ASICs.

The invention claimed is:

1. A method for mitigating detector position errors in an imaging system; wherein the imaging system comprises at least one detector-connected to a gantry, and rotatable about the gantry; and wherein the imaging system is a member of a class of imaging systems having the same detector/gantry configuration, the method comprising:
   determining a set of angle-dependent gantry deflection function (GDF) of the class;
   determining an angle-independent delta gantry deflection function vector ($\Delta$GDF) of the system;
   applying the GDF and $\Delta$GDF in image reconstruction in the imaging system.

2. The method of claim 1 wherein:
   each angle-dependent GDF comprises a zero-mean function.

3. The method of claim 2 wherein:
   each angle-dependent GDF further comprises a collimator factor.

4. The method of claim 1 wherein:
   the $\Delta$GDF is determined with respect to a plurality of point sources using the imaging system.

5. The method of claim 3 wherein:
   the plurality of point are contained in a fixture, and
   the $\Delta$GDF with respect to the plurality of point sources using the imaging system is determined with respect to a reference point on the fixture and the Euler angles of the point with respect to the imaging system coordinate system.

6. A computer program product for mitigating detector position errors in an imaging system; wherein the imaging system comprises at least one detector connected to a gantry, and rotatable about the gantry; and wherein the imaging system is a member of a class of imaging systems having the same detector/gantry configuration, the computer program product comprising:
   a least one computer readable medium; and
   at least one program module,
      stored on the at least one medium, and
      operative, upon execution by at least one processor for:
         determining an angle-dependent gantry deflection function (GDF) of the class;
         determining an angle-independent delta gantry deflection function vector ($\Delta$GDF) of the system;
         applying the GDF and $\Delta$GDF in image reconstruction in the imaging system.

7. The computer program product claim 6 wherein:
   each angle-dependent GDF comprises a zero-mean function.

8. The computer program product of claim 7 wherein:
   each angle-dependent GDF further comprises a collimator factor.

9. The computer program product of claim 6 wherein:
   the $\Delta$GDF is determined with respect to a plurality of point sources using the imaging system.

10. The computer program product of claim 8 wherein:
   the plurality of point are contained in a fixture, and
   the $\Delta$GDF with respect to the plurality of point sources using the imaging system is determined with respect to a reference point on the fixture and the Euler angles of the point with respect to the imaging system coordinate system.

11. An imaging system comprising at least one detector connected to a gantry, and rotatable about the gantry; and wherein the imaging system is a member of a class of imaging systems having the same detector/gantry configuration, assembled by the following process for mitigating detector position errors in the imaging system:
   determining an angle-dependent gantry deflection function (GDF) of the class;
   determining an angle-independent delta gantry deflection function vector ($\Delta$GDF) of the system;
   applying the GDF and $\Delta$GDF in image reconstruction in the imaging system.

12. The imaging system of claim 11 wherein:
   each angle-dependent GDF comprises a zero-mean function.

13. The imaging system of claim 12 wherein:
   each angle-dependent GDF further comprises a collimator factor.

14. The imaging system of claim 11 wherein:
   the $\Delta$GDF is determined with respect to a plurality of point sources using the imaging system.

15. The imaging system of claim 13 wherein: the plurality of point are contained in a fixture, and the $\Delta$GDF with respect to the plurality of point sources using the imaging system is determined with respect to a reference point on the fixture and the Euler angles of the point with respect to the imaging system coordinate system.

* * * * *